(12) United States Patent
Qi et al.

(10) Patent No.: US 7,493,219 B1
(45) Date of Patent: Feb. 17, 2009

(54) METHOD OF DISCRIMINATING PARTICLE GROUPS AND PARTICLE ANALYZER

(75) Inventors: Huan Qi, Shenzhen (CN); Wenjun Tong, Shenzhen (CN)

(73) Assignee: Shenzhen Mindray Bio-Medical Electronics Co., Shenzhen (CN)

( * ) Notice: Subject to any disclaimer, the term of this patent is extended or adjusted under 35 U.S.C. 154(b) by 0 days.

(21) Appl. No.: 11/965,642

(22) Filed: Dec. 27, 2007

(30) Foreign Application Priority Data

Sep. 13, 2007 (CN) .................. 2007 1 0077096

(51) Int. Cl.
*G06K 9/46* (2006.01)

(52) U.S. Cl. .................. 702/26; 702/19; 702/21; 702/22; 702/23; 702/24; 702/25; 702/27; 356/39; 600/462; 600/463; 600/464; 600/465; 600/466; 600/467; 600/468; 250/573; 250/574; 250/575; 250/576

(58) Field of Classification Search .................. 702/19, 702/21–27; 356/39; 600/462–468; 250/573–576
See application file for complete search history.

(56) References Cited

U.S. PATENT DOCUMENTS

| | | | |
|---|---|---|---|
| 4,202,625 A | 5/1980 | Weiner et al. | |
| 4,933,884 A | 6/1990 | Lorenz | |
| 5,532,943 A * | 7/1996 | Asano et al. | ............ 702/21 |
| 6,522,781 B1 * | 2/2003 | Norikane et al. | ............ 382/203 |

FOREIGN PATENT DOCUMENTS

| | | |
|---|---|---|
| CN | 1091830 | 9/1994 |
| CN | 1945326 | 4/2007 |
| CN | 101000306 | 7/2007 |
| JP | 2042357 | 2/1990 |
| JP | 2042358 | 2/1990 |
| JP | 1945326 | 4/2007 |
| WO | WO9716718 | 5/1997 |

* cited by examiner

*Primary Examiner*—Tung S Lau
*Assistant Examiner*—Sujoy K Kundu
(74) *Attorney, Agent, or Firm*—Vista IP Law Group, LLP

(57) ABSTRACT

A method for discriminating particle groups comprises generating, by a particle analyzer, a particle characteristic distribution histogram in which the abscissa indicates respective channels for representing the characteristics of the particles, and the ordinate indicates the particle count; setting a valid area selection height in the particle characteristics distribution histogram; and generating an equivalent negative histogram based on the set height and the particle characteristic distribution histogram.

24 Claims, 7 Drawing Sheets

METHOD OF DISCRIMINATING PARTICLE GROUPS AND PARTICLE ANALYZER

RELATED APPLICATIONS

This application claims priority to Chinese Patent Application No. 200710077096.1, filed Sep. 13, 2007, which is incorporated herein by reference.

TECHNICAL FIELD

The present disclosure relates to a method and particle analyzer for discriminating particle groups.

SUMMARY

Statistical solutions are applied to a method for discriminating particle groups, including the generation of a particle characteristics distribution histogram and an equivalent negative histogram.

DETAILED DESCRIPTION OF PREFERRED EMBODIMENTS

A hematology analyzer, which is an instrument for counting and classifying human blood cells, is widely applied in clinic and laboratory settings. A hematology analyzer mainly provides testing parameters such as white blood cell (WBC) count, red blood cell (RBC) count, mean cell volume (MCV), platelet (PLT) count, mean platelet volume (MPV) and the like. These testing results of a hematology analyzer are very important references for clinical doctors to diagnose a patient's condition, and thereby they are required to be accurate and reliable. The accurate measurement of platelets is one of the important characteristics that the hematology analyzer should have. Currently, most of the hematology analyzers utilize a conventional measurement method in which platelets are measured by an electrical impedance method.

Figure 1:
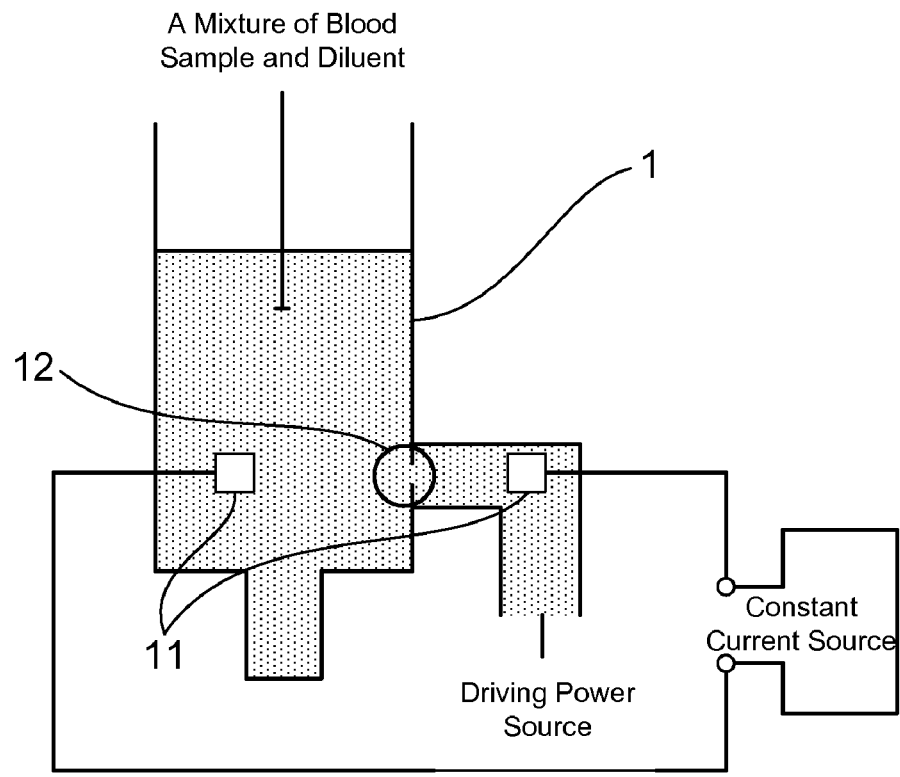
FIG. 1 is a schematic diagram showing the structure of a hematology analyzer.

As shown in FIG. 1, a hematology analyzer generally comprises a counting bath 1, a driving power source, a constant current source and an analyzing circuit. Further, electrodes 11 and an aperture 12 are provided within the counting bath 1, and the constant current source provides constant current to the electrodes 11. The conventional measurement method of the hematology analyzer is described below. A blood sample is added into a certain amount of diluent, which is electrically conductive and used to maintain the cell morphology. Then, this mixture is driven to pass through the aperture 12 by the driving power source.

Figure 2:
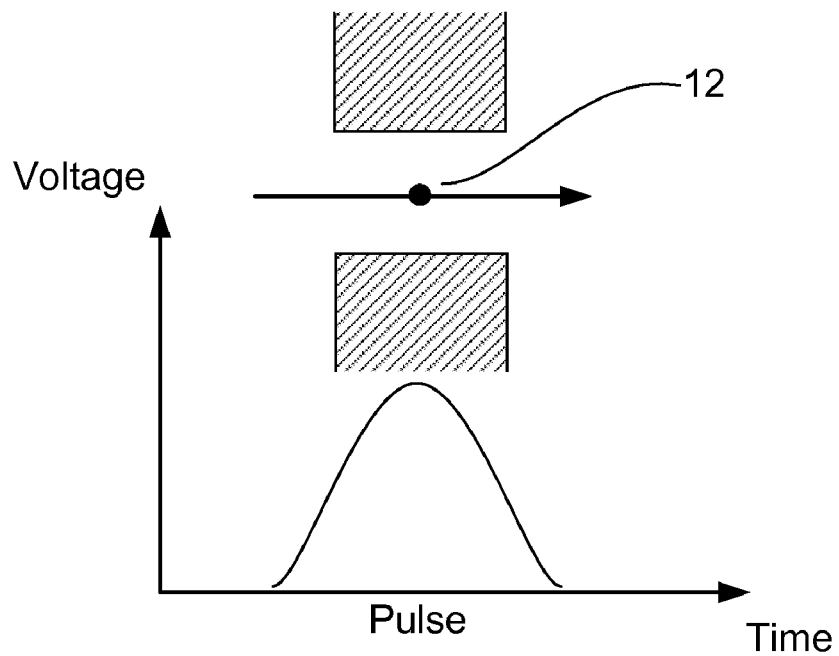
FIG. 2 shows voltage pulses generated when a blood cell particle passes through an aperture.

Because cells have low conductivity, the equivalent electrical impedance within the aperture 12 becomes larger when a cell is passing through the aperture, as illustrated in FIG. 2. Under a constant current source, the change in voltage is proportional to the change in impedance; that is, the voltage waveform reflects impedance change during the process of a particle passing through the aperture. As a result, a voltage pulse will be generated when a particle is passing through the aperture, and the height of such a voltage pulse indicates the volume size of the particle.

Figure 3:
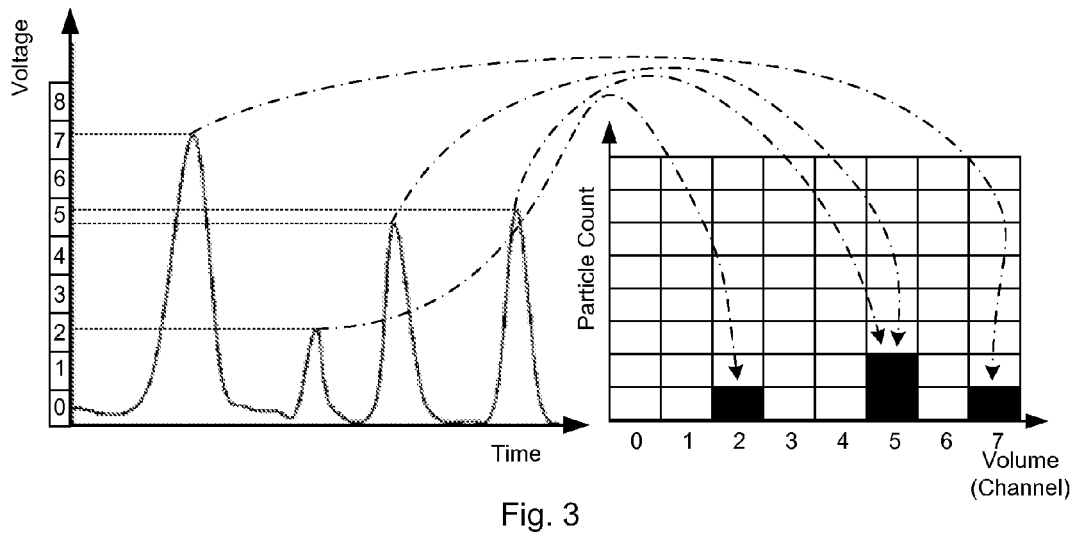
FIG. 3 is a schematic diagram showing the formation of a cell volume distribution histogram.

As illustrated in FIG. 3, the analyzing circuit statistically counts all of the cells, based on their volume size, into individual bars of a cell volume distribution histogram, each bar corresponding to a respective channel. In this way, a cell volume distribution histogram is generated, in which the abscissa indicates the respective channels (corresponding to cell volume) and the ordinate indicates the number of cells.

The mixture driven through the aperture contains three kinds of particles: white blood cells, red blood cells and platelets. No matter which one of those cells is passing through the aperture, a pulse is generated. From the pulses, therefore, what can be determined is not the kind of each cell, but only the distribution and the number of all cells in the blood sample. The volume of a white blood cell in blood is larger than the volume of a red blood cell or platelet, and the number of white blood cells is far less than that of red blood cells and platelets. For this reason, the influence of the white blood cells can be left out of account in the measurement of platelets.

Because it is difficult to separate platelets from red blood cells using only reagents, red blood cells and platelets are typically measured synchronously in the hematology analyzer. In normal conditions, the volume of a red blood cell (RBC) is larger than that of a platelet (PLT); RBC count is bigger, and PLT count is smaller. The PLT count, for a healthy body, is one-twentieth of RBC count. The distribution of RBC is mainly in the range of 40 femtoliters (fL)~130 fL (Note: femtoliter is a unit of volume, 1 fL=1 L/$10^{15}$), and the distribution of PLT is mainly in the range of 2 fL~25 fL. Therefore, the blood cell distribution obtained by the hematology analyzer normally includes two groups: one is the PLT group distributed in the range of smaller volume, and the other is the RBC group distributed in the range of larger volume.

Figure 4:
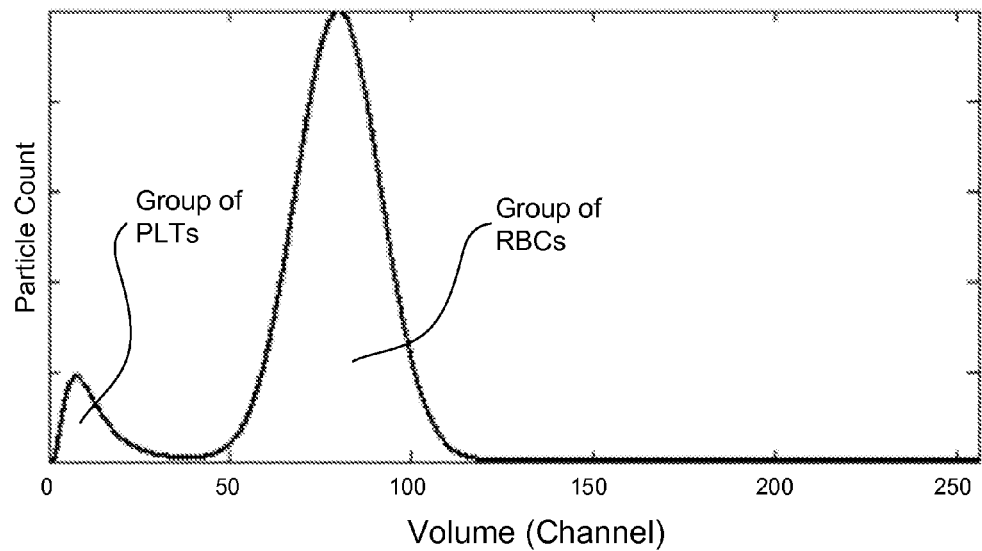
FIG. 4 is a schematic diagram showing the distribution of platelets and red blood cells.

FIG. 4 is a schematic diagram showing the distribution of PLT and RBC. The aim in discriminating PLT from RBC is to find out the lowest point of a trendline of the distribution histogram between the peaks of RBC and PLT. The position of the lowest point is the dividing line between the two groups.

For a normal blood sample, in one of the methods of discriminating PLTs from RBCs by the hematology analyzer, the cells above a certain fixed threshold of volume are considered as RBCs, and those below the threshold of volume are considered as PLTs. The present disclosure refers to this method as the "fixed method," and similar methods are disclosed in U.S. Pat. No. 4,202,625, which is incorporated herein by reference.

For abnormal blood samples, however, the distribution range of RBCs and PLTs may be expanded and overlapped with each other, or several kinds of different distributions may occur. In these cases, the method with a fixed dividing line is unable to meet the requirements for accurately measuring the abnormal samples. To avoid this phenomenon, a method is provided to determine the lowest point in the distribution histogram between the peaks of the two cell groups as the dividing line of the two groups, which is referred to as the "lowest point floating method."

The above-mentioned two methods have respective benefits. The "fixed method" has stable features, but is not adapted to abnormal samples. The "lowest point floating method," on the other hand, may be adapted to most normal and abnormal samples, but is short of stability for the abnormal samples having a lower PLT concentration; that is, there are great differences between multiple results obtained from the measurement of the same sample.

The deficiencies of both methods mentioned above may be overcome by a method for discriminating particle groups and a particle analyzer capable of providing stable and accurate measurements as briefly summarized below.

In one embodiment, a method for discriminating particle groups comprises generating a particle characteristic distribution histogram for particles within a sample to be measured, based on characteristics of the particles and particle count, where a first direction coordinate of the particle characteristic distribution histogram indicates channels for representing the characteristics of the particles, and a second direction coordinate indicates the particle count.

The method also includes setting a valid area selection height in the particle characteristics distribution histogram, and generating an equivalent negative histogram based on the set height and the particle characteristic distribution histogram, where a height value of a bar in the equivalent negative histogram for a certain channel equals the valid area selection height minus a height value of a bar in the particle characteristic histogram for said channel.

The method further includes processing the equivalent negative histogram by using an equation $$M_k = \frac{\int x \cdot g(f(x)) dx}{\int g(f(x)) dx}$$

to obtain a dividing line between the particle groups, where $M_k$ is the dividing line between the particle groups; x is a channel value in the equivalent negative histogram; f(x) is a height value of a bar in the equivalent negative histogram for channel x; and g(•) is a processing function with the following features:

$\forall x \geq y \geq 0, g(x) \geq g(y) \geq 0$ $\forall x < 0, g(x) = 0$.

In one embodiment, the characteristic of particles is the volume size of the particles. The valid area selection height is lower than a maximum of the particle count for a particle group having fewer particles. The equivalent negative histogram has the same number of channels as the particle characteristic distribution histogram, and each of the channels in the equivalent negative histogram has the same meaning as that in the particle characteristic distribution histogram. The equivalent negative histogram only has valid values in a dividing area, and has zeros for other channels.

In one configuration, the sample to be measured is a blood sample, the particle analyzer is a hematology analyzer and the particle groups to be discriminated includes a group of platelets and a group of red blood cells, or includes a group of lymphocytes and a group of granulocytes. However, those of skill in the art will recognize that other types of particles may be analyzed using similar techniques.

The method may further comprise an initial step of driving a mixture of the sample to be measured and a diluent through an aperture by a driving power source, a step of capturing a voltage pulse by the particle analyzer when each particle is passing through the aperture, and a step of calculating, by the particle analyzer, the volume of each particle and calculating the particle count corresponding to the same volume based on the captured voltage pulses.

The present disclosure also relates to a particle analyzer for discriminating particle groups. In one embodiment, the particle analyzer includes a histogram generating unit for generating a particle characteristic distribution histogram for particles within a sample to be measured based on characteristics of the particles and particle count, where a first direction coordinate of the particle characteristic distribution histogram indicates channels for representing the characteristics of particles, and a second direction coordinate indicates the particle count. The particle analyzer further includes a valid area selection height generation unit for setting a valid area selection height in the particle characteristic distribution histogram. The particle analyzer also includes an equivalent negative histogram generation unit for generating an equivalent negative histogram based on the valid area selection height and the particle characteristic distribution histogram, where a height value of a bar in the equivalent negative histogram for a certain channel is equal to the valid area selection height minus a height value of a bar in the particle characteristic histogram for said channel. The particle analyzer also includes a dividing line determination unit for processing the equivalent negative histogram by using an equation $$M_k = \frac{\int x \cdot g(f(x)) dx}{\int g(f(x)) dx}$$

to obtain a dividing line between the particle groups, where, $M_k$ is the dividing line between the particle groups; x is a channel value in the equivalent negative histogram; f(x) is a height value of a bar in the equivalent negative histogram for channel x; and g(•) is a processing function with the following features:

$\forall x \geq y \geq 0, g(x) \geq g(y) \geq 0$ $\forall x < 0, g(x) = 0$.

In one embodiment, the characteristic of particles is the volume size of particles, and the valid area selection height is lower than a maximum of the particle count for a particle group having fewer particles.

In one implementation, a particle analyzer includes an aperture structure through which a mixture of a sample to be measured and an electrically conductive diluent is driven to pass by a driving power source. The particle analyzer may also include a data capturing unit for capturing a voltage pulse when each particle is passing through the aperture. The particle analyzer may further include a data statistic calculation unit for calculating, based on the captured voltage pulses, the volume of each particle and the particle count corresponding to the same volume.

In one embodiment, the particle analyzer includes a histogram generating unit for generating a particle characteristic distribution histogram for particles within a sample to be measured based on characteristics of the particles and particle count, where a first direction coordinate of the particle characteristic distribution histogram indicates channels for representing the characteristics of particles, and a second direction coordinate indicates the particle count.

The particle analyzer may also include a valid area selection height generation unit for setting a valid area selection height in the particle characteristic distribution histogram.

In one configuration, the particle analyzer may include an equivalent negative histogram generation unit for generating an equivalent negative histogram based on the valid area selection height and the particle characteristic distribution histogram, where a height value of a bar in the equivalent negative histogram for a certain channel equals the valid area selection height minus a height value of a bar in the particle characteristic histogram for said channel.

The particle analyzer may further include a dividing line determination unit for processing the equivalent negative histogram by using an equation $$M_k = \frac{\int x \cdot g(f(x)) dx}{\int g(f(x)) dx}$$

to obtain a dividing line between the particle groups, where, $M_k$ is the dividing line between the particle groups; x is a channel value in the equivalent negative histogram; f(x) is a height value of a bar in the equivalent negative histogram for channel x; and g(•) is a processing function with the following features:

$\forall x \geq y \geq 0, g(x) \geq g(y) \geq 0$ $\forall x < 0, g(x) = 0$.

The disclosed method will not be impacted by the details of the particle characteristic distribution histogram, but will focus on the features in the whole trend of the distribution. Therefore, the disclosed method is much more stable than the conventional floating method and can provide stable measurement. The disclosed method overcomes the deficiencies in processing ability when the "fixed method" is used to measure a special blood sample. The disclosed method further has an auto-floating ability for the different samples with different distributions, so as to be capable of providing accurate measurement on the basis of keeping stability. The disclosed method is able to discriminate particle groups based on statistics. The disclosed method has an auto-floating ability to automatically adjust the dividing line with reference to the sample's characteristics, has strong stability and good accuracy, and is capable of obtaining a much better effect of discrimination and increasing the ability to be adapted to the abnormal samples. The disclosed method is very suitable for discriminating platelets from red blood cells, and may further provide much more stable platelet measurement for the hematology analyzer, while maintaining accuracy.

In one embodiment, statistical solutions are applied to a method for discriminating platelets from red blood cells. According to the present disclosure, the dividing line between platelets and red blood cells may be determined by first defining a series of statistics based on features of a problem to be solved, and then calculating a statistic of a particle group, which is represented by a special area in an equivalent negative histogram for platelets and red blood cells. By using the method of the present disclosure, platelets may be measured accurately and reliably.

Figure 5:
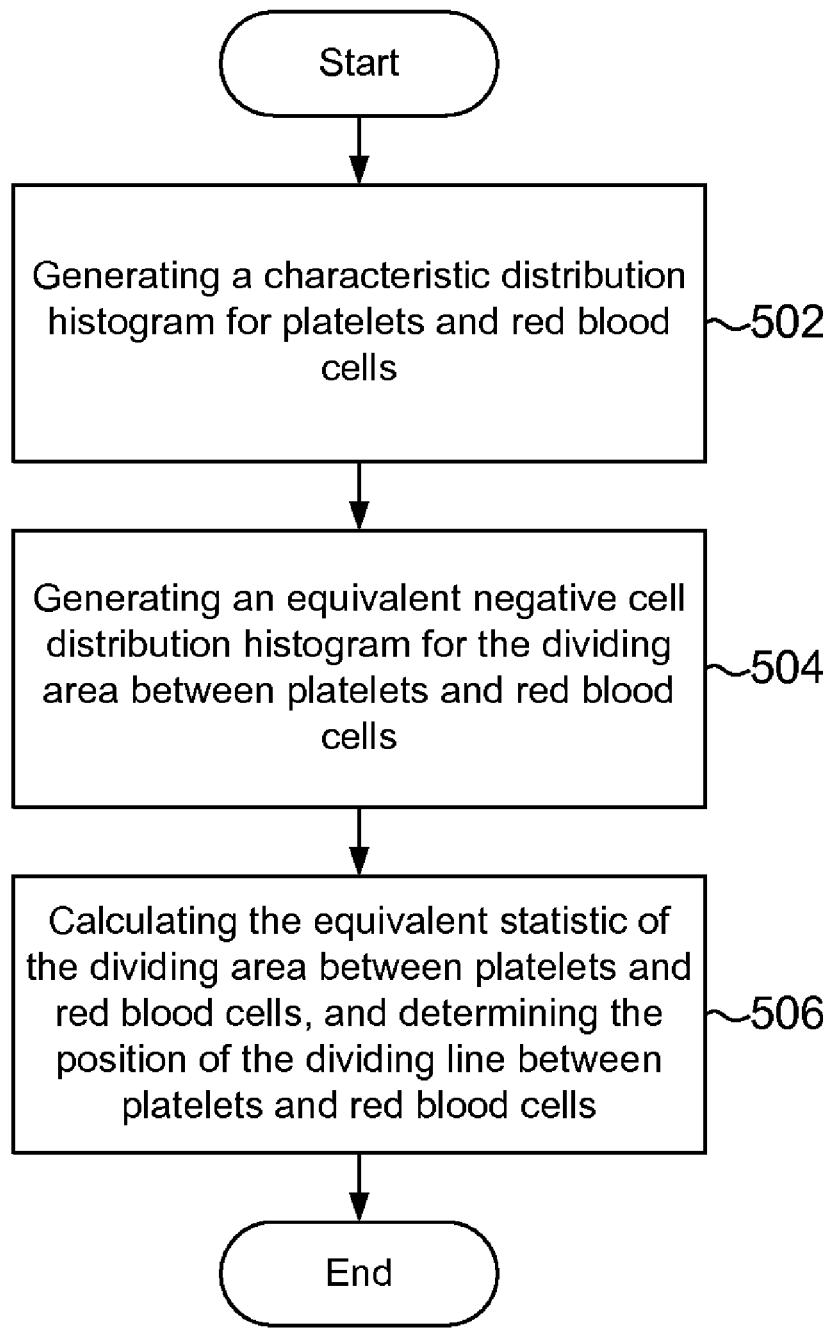
FIG. 5 is a flow chart of a method for discriminating particle groups.
Figure 6A:
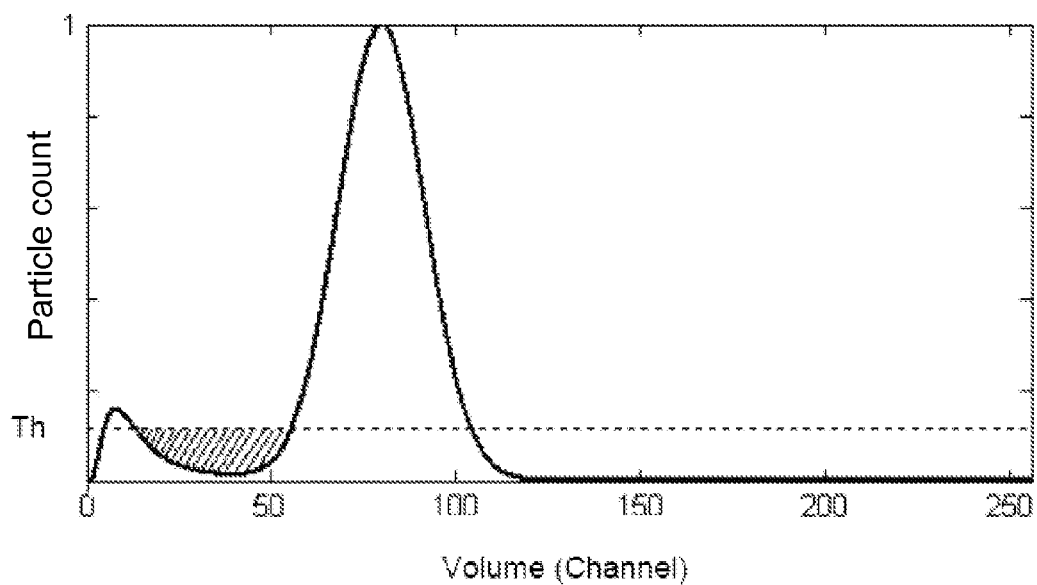
FIG. 6a is a characteristic distribution histogram for platelets and red blood cells, which is obtained during a processing procedure.

Referring to FIG. 5, one embodiment of a method for discriminating platelets from red blood cells is described. A mixture of a blood sample and a diluent is driven by a driving power source to pass through an aperture. Thereafter, a hematology analyzer (one kind of particle analyzer) detects the particles passing through the aperture, based on the electric impedance changes at the aperture. The hematology analyzer captures each voltage pulse generated when each particle is passing through the aperture. Based on the captured voltage pulses, the hematology analyzer statistically calculates the particles' characteristics and the number of the particles relevant thereto, so as to generate 502 a characteristic distribution histogram for platelets and red blood cells. FIG. 6a shows a characteristic distribution histogram for platelets and red blood cells, in which a first direction coordinate (abscissa) indicates the characteristic channels of blood cells (in the present embodiment, the cell volume is considered as the characteristic of the blood cells, because platelets are clearly different from red blood cells in volume), and a second direction coordinate (ordinate) indicates the number of particles or particle count.

Figure 6B:
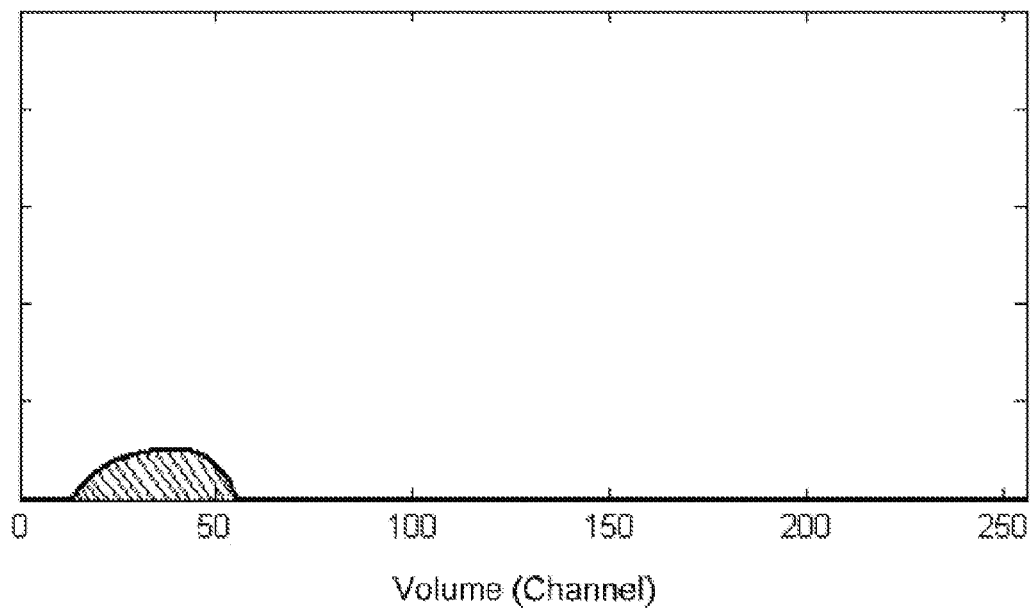
FIG. 6b is an equivalent negative histogram for platelets and red blood cells, which is obtained during a processing procedure.

As shown in FIGS. 6a and 6b, a certain height is set in the characteristic distribution histogram for platelets and red blood cells, and the certain height is referred to as valid area selection height (denoted as Th). Then, said height is used together with the characteristic distribution histogram for platelets and red blood cells to generate 504 a virtual particle distribution histogram, which is referred to as an equivalent negative cell distribution histogram for a dividing area between platelets and red blood cells, and is also called as "an equivalent negative histogram," for short.

The method of generating the equivalent negative histogram may be described as the following equation. A height value of a bar in the equivalent negative histogram for a certain channel equals the valid area selection height (Th) minus a height value of a bar in the characteristic distribution histogram for said channel. The equivalent negative histogram represents a group of cells, which is referred to as the equivalent negative particle group for the dividing area between platelets and red blood cells, and is denoted as a negative particle group. The valid area selection height should be lower than the maximum of particle count for a particle group with fewer particles, that is, being less than the maximum of the particle count in the group of platelets.

The equivalent negative histogram has the same number of channels as that of the characteristic distribution histogram for blood cells, and the same channel of both histograms represents the same volume size of particles. When the equivalent negative histogram is generated, only the part of the histogram for the dividing area between the group of platelets and the group of red blood cells is selected. That is, the equivalent negative histogram has valid values only in the dividing area and zero values for other channels.

The equivalent negative histogram is processed using an equation as below, to calculate 506 a certain statistic for the equivalent negative particle group, which is also called an equivalent statistic for the dividing area between platelets and red blood cells. This equivalent statistic is the dividing line between the group of platelets and the group of red blood cells. The equation is shown below:

$$M_k = \frac{\int x \cdot g(f(x))dx}{\int g(f(x))dx} \qquad 5$$

where $M_k$ is the equivalent statistic for the dividing line between platelets and red blood cells, that is, the dividing line between the group of platelets and the group of red blood cells; x represents a channel value in the equivalent negative histogram (corresponding to the volume size of a cell); f(x) indicates a height value of a bar in the equivalent negative histogram for the $x_{th}$ channel; and g(•) is a processing function, which may ideally have the following features:

$$\forall x \geq y \geq 0, g(x) \geq g(y) \geq 0$$

$$\forall x < 0, g(x) = 0.$$

The platelets and red blood cells may be accurately measured by using this equivalent statistic for the dividing area.

In general, the object of measuring the dividing line between platelets and red blood cells is to definitely find out the lowest point of a trendline in a dividing area between the two groups, that is, the group of platelets and the group of red blood cells. After transforming the dividing line between platelets and red blood cells into an equivalent negative particle distribution histogram, this object is correspondingly transformed from finding the lowest point of the trendline in the dividing area between platelets and red blood cells into finding the highest point of a trendline in the equivalent negative particle histogram. $M_k$ is designed to statistically represent the highest point of the virtual negative histogram.

The statistic $M_k$ is shown below:

$$M_k = \frac{\int x \cdot g(f(x))dx}{\int g(f(x))dx}$$

The above equation may be transformed into a discrete form, and may be expanded as:

$$M_k = \frac{\sum_{i=1}^{N} i * g(f_i)}{\sum_{i=1}^{N} g(f_i)} = \frac{1 * g(f_1) + 2 * g(f_2) + L \; i * g(f_i) + L + (N-1) * g(f_{N-1}) + N * g(f_N)}{\sum_{i=1}^{N} g(f_i)} =$$

$$a_1 * 1 + a_2 * 2 + L \; a_i * i + L + a_{N-1} * (N-1) + a_N * N$$

where $$a_i = \frac{g(f_i)}{\sum_{i=1}^{N} g(f_i)},$$

N is the total number of the channels in the equivalent negative histogram; and $f_i$ is a height value of a bar in the equivalent negative histogram for the $i_{th}$ channel. It is clear that $$\sum_{i=1}^{N} a_i = 1.$$

From the equation shown above, it can be seen that $M_k$ is substantially a weighted sum for a series of digital channels 1-N, and the weight for each channel is determined by a height value of a bar in the equivalent negative histogram for said channel. For example, $a_i$, which is a weight of the $i_{th}$ channel, is obtained by a resultant value after a height value of the bar in the histogram for the $i_{th}$ channel is processed by the function g(•), and by a sum of the resultant values for all of the channels in the whole histogram after being processed by the function g(•). Those of skill in the art will note that the function g(•) is a monotonously increasing function, i.e., $\forall x \geq y \geq 0, g(x) \geq g(y) \geq 0$ This means the weight $a_i$ has a larger value at the channel with a higher point in the histogram, or the $i_{th}$ channel occupies a higher weight ratio in $M_k$. Thus the obtained $M_k$ is very close to the highest point of the trendline in the dividing area between the group of platelets and the group of red blood cells.

Figure 7A:
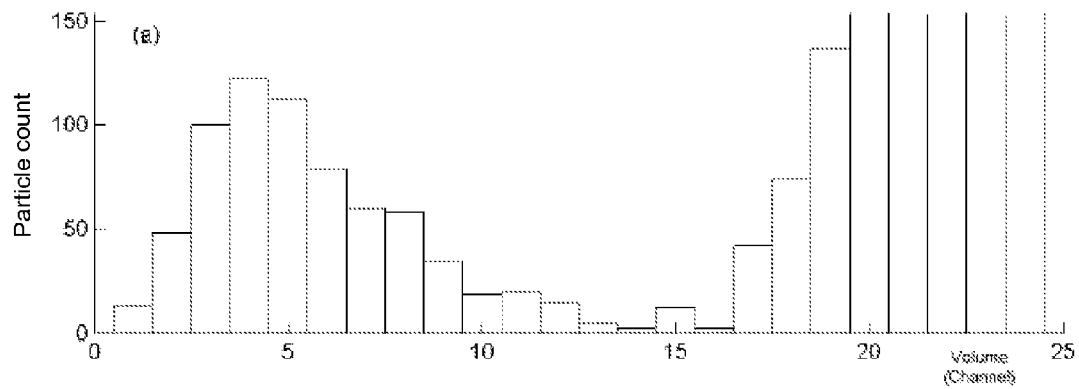
FIG. 7a is a histogram of a dividing area between platelets and red blood cells in a certain sample.
Figure 7B:
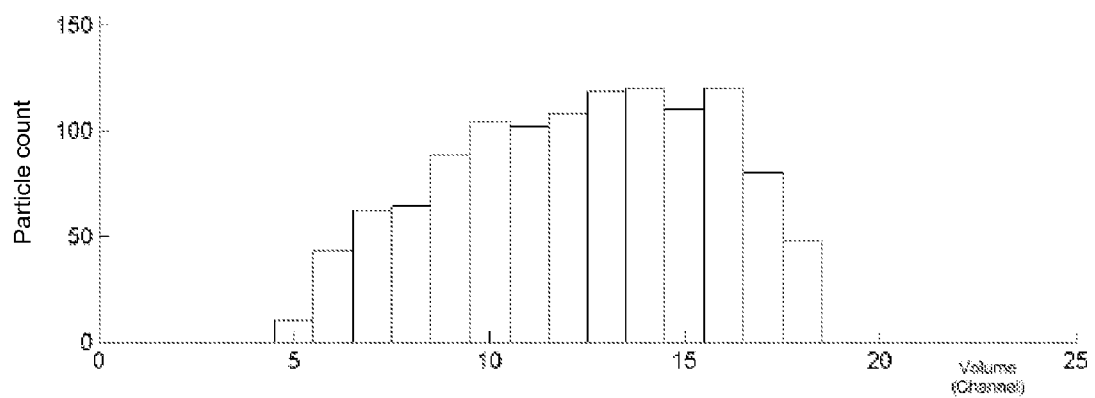
FIG. 7b is an equivalent negative histogram of a dividing area between platelets and red blood cells in a certain sample.

FIG. 7a shows a histogram for a dividing area between platelets and red blood cells in a blood sample. According to the method as mentioned above, the equivalent negative histogram may be obtained as shown in FIG. 7b. From FIG. 7b, it can be seen that the ideal dividing line between platelets and red blood cells should be at the highest point of the trendline in the histogram, i.e., at the Channel 14.

Table 1 lists the particle count for each of the channels. (Note that the particle count for each of the channels after Channel 22 is omitted, because each is zero.)

TABLE 1

| Volume (Channel, i) | 1 | 2 | 3 | 4 | 5 | 6 | 7 | 8 | 9 | 10 | 11 |
|---|---|---|---|---|---|---|---|---|---|---|---|
| (Equivalent negative histogram) Particle count (hi) | 0 | 0 | 0 | 0 | 10 | 43 | 62 | 64 | 88 | 104 | 102 |
| Volume (Channel, i) | 12 | 13 | 14 | 15 | 16 | 17 | 18 | 19 | 20 | 21 | 22 |
| (Equivalent negative histogram) Particle count (hi) | 108 | 118 | 120 | 110 | 120 | 80 | 48 | 0 | 0 | 0 | 0 |

Herein, the $g(x)=\sqrt{e^{x/8}}$ is provided as an example, and thereby the weight value $a_i$ for each of the channels may be calculated as follows (see Table 2):

TABLE 2

| Volume (Channel, i) | 1 | 2 | 3 | 4 | 5 |
|---|---|---|---|---|---|
| $a_i$ | 0.000 | 0.000 | 0.000 | 0.000 | 0.000 |
| Volume (Channel, i) | 6 | 7 | 8 | 9 | 10 |
| $a_i$ | 0.002 | 0.005 | 0.006 | 0.028 | 0.075 |
| Volume (Channel, i) | 11 | 12 | 13 | 14 | 15 |
| $a_i$ | 0.067 | 0.097 | 0.181 | 0.205 | 0.110 |
| Volume (Channel, i) | 16 | 17 | 18 | 19 | 20 |
| $a_i$ | 0.205 | 0.017 | 0.002 | 0.000 | 0.000 |
| Volume (Channel, i) | 21 | 22 | \ | \ | \ |
| $a_i$ | 0.000 | 0.000 | \ | \ | \ |

Based on the equation above, it can be calculated that:

$$M_k = a_1 * 1 + a_2 * 2 + L\, a_i * i + L + a_{N-1} * (N-1) + a_N * N =$$
$$0.000 * 1 + 0.000 * 2 + L 0.181 * 13 + L + 0.000 * 21 + 0.000 * 22 \approx 13.5$$

Figure 8:
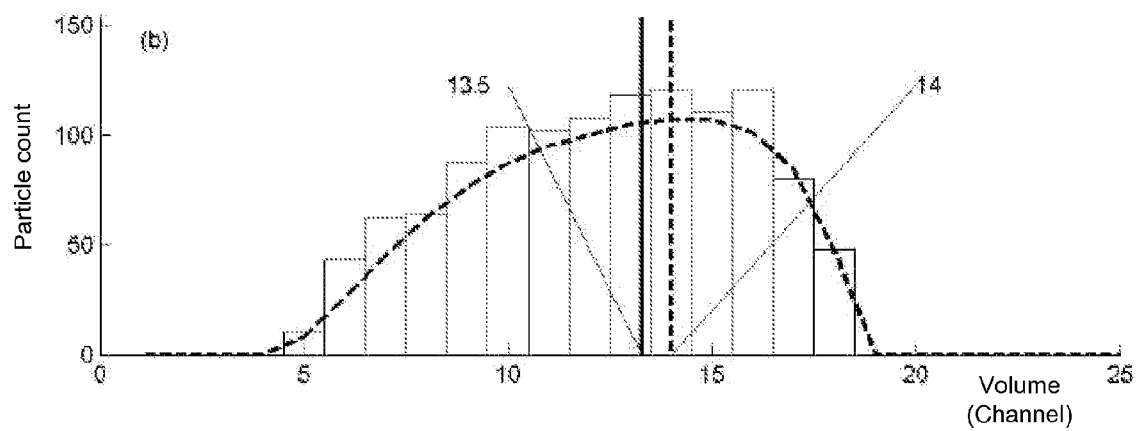
FIG. 8 is a schematic diagram showing the dividing line between platelets and red blood cells, which is obtained by processing a certain sample.

The calculated dividing line between platelets and red blood cells is 13.5, which is surprisingly close to the ideally expected value. Thus it can be seen that disclosed method may achieve very high accuracy. FIG. 8 is a schematic diagram showing the dividing line between platelets and red blood cells, calculated using the techniques described above.

Figure 9:
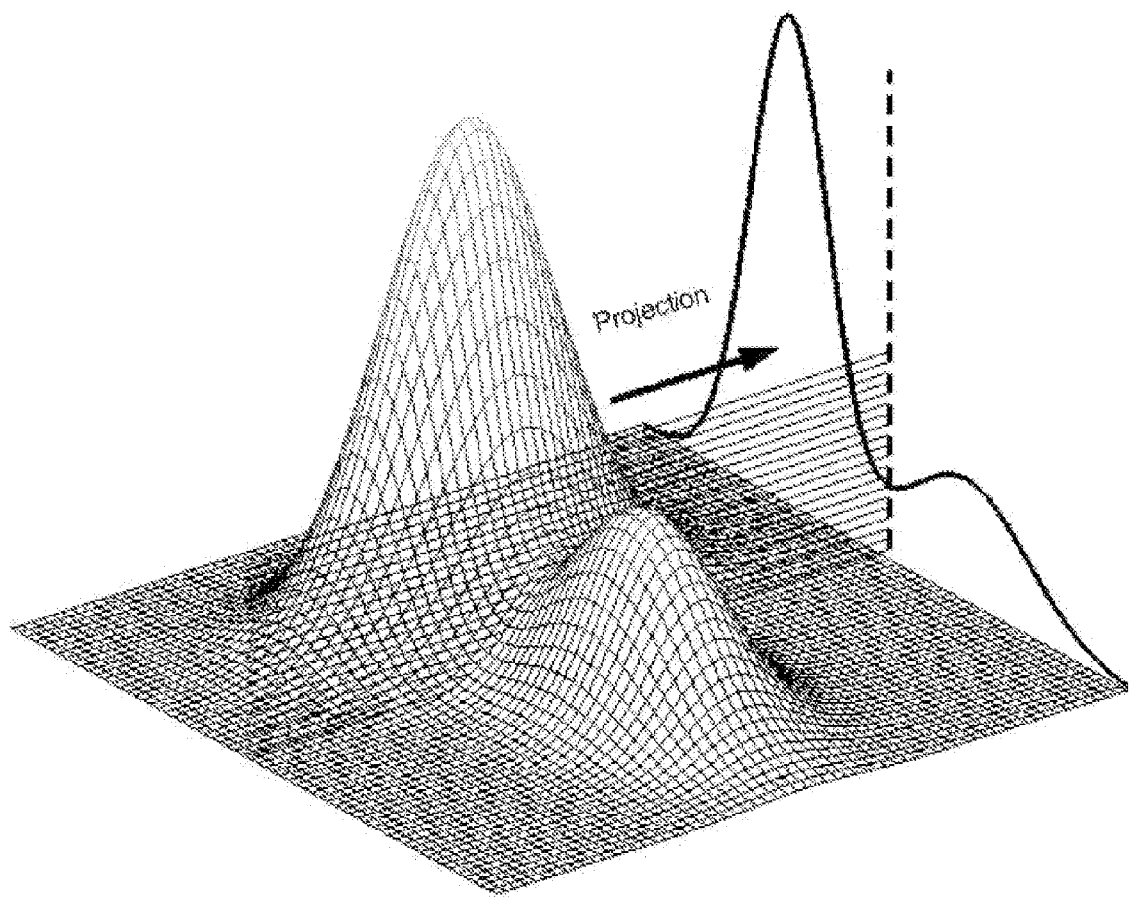
FIG. 9 is an example of an application where a method for discriminating particle groups is expanded to two dimensions.

The disclosed method may also be applied to accurately and reliably classifying two or more groups of particles, which have different characteristics, in addition to discriminating platelets from red blood cells. For example, in a hematology analyzer with an electrical impedance measurement, the disclosed method may be used to discriminate lymphocytes from granulocytes. In this example, the characteristic of particles may be determined as not only the volume of particles, but also the complexity of nucleolus, the information of DNA/RNA, the laser absorption characteristic of particles, the radio absorption characteristic of particles, the fluorescence absorption characteristic of particles, and other kinds of parameters, as long as the groups of particles to be discriminated have obvious differences in these characteristics. Furthermore, the disclosed method may be expanded from the classification based on one-dimensional characteristics to the one based on two or more dimensional characteristics, so that the groups of particles that have obvious differences in characteristics may be discriminated from each other more accurately and reliably. For example, as shown in FIG. 9, when the particle analyzer obtains a particle distribution diagram having two or more dimensions after analysis, it may project the particle distribution diagram having two or more dimensions, and then use the projected outline as an input (i.e., the particle characteristic distribution histogram), where the selected direction for projection is a direction in which the characteristic differences are relatively obvious between the groups of particles to be discriminated. The subsequent process is the same as that for the above embodiment, and thereby the detailed description is omitted.

Figure 10:
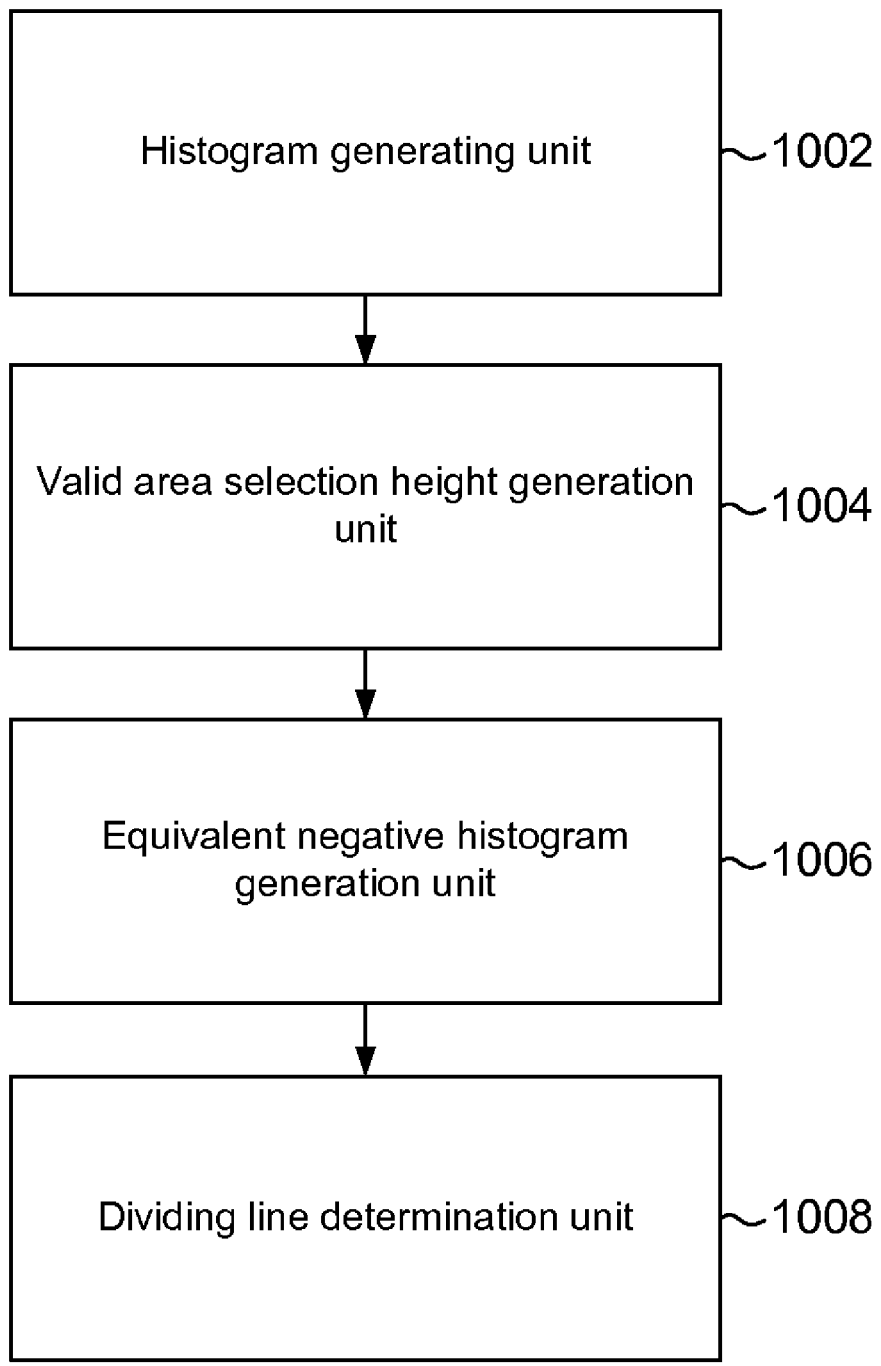
FIG. 10 is a schematic diagram showing the structure of a particle analyzer.

FIG. 10 shows an apparatus for performing the method as above mentioned, i.e., a particle analyzer for discriminating particle groups. As shown in FIG. 10, the particle analyzer comprises a histogram generating unit 1002, a valid area selection height generation unit 1004, an equivalent negative histogram generation unit 1006, and a dividing line determination unit 1008. The output of the histogram generating unit 1002 is connected with the input of the valid area selection height generation unit 1004, the output of the valid area selection height generation unit 1004 is connected with the input of the equivalent negative histogram generation unit 1006, and the output of the equivalent negative histogram generation unit 1006 is connected with the input of the dividing line determination unit 1008.

The histogram generation unit 1002 is used to generate a characteristic distribution histogram for particles within a sample to be measured, based on characteristics of the particles and particle count, where a first direction coordinate of the particle characteristic distribution histogram indicates channels for representing the characteristics of particles, and a second direction coordinate indicates the particle count.

The valid area selection height generation unit 1004 is configured to set a valid area selection height in the particle characteristic distribution histogram. The equivalent negative histogram generation unit 1006 is configured to generate an equivalent negative histogram based on the set valid area selection height and the particle characteristic distribution histogram, where a height value of a bar in the equivalent negative histogram for a certain channel equals the valid area selection height minus a height value of a bar in the particle characteristic histogram for said channel.

The dividing line determination unit 1008 is configured to process the equivalent negative histogram by using an equation:

$$M_k = \frac{\int x \cdot g(f(x)) dx}{\int g(f(x)) dx}$$

to obtain a dividing line between the particle groups, where $M_k$ is the dividing line between the particle groups; x is a channel value in the equivalent negative histogram; f(x) is a height value of a bar in the equivalent negative histogram for channel x; and g(•) is a processing function with the following features:

$\forall x \geq y \geq 0, g(x) \geq g(y) \geq 0$ $\forall x < 0, g(x) = 0.$

The above particle analyzer may further comprise an aperture structure, through which a mixture of a sample to be measured and an electrically conductive diluent is driven to pass by a driving power source; a data capturing unit, for capturing a voltage pulse generated when each particle is passing through the aperture; and a data statistic calculation unit, for calculating the volume of each particle and particle count corresponding to the same volume based on the captured voltage pulses.

The disclosed method may embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

Although the disclosed method and particle analyzer have been described in conjunction with specific embodiments, it is evident that many alternatives, modifications and variations will be understood to those skilled in the art in light of the foregoing description. Accordingly, it is intended to embrace all such alternatives, modifications and variations as fall within the scope of the appended claims.

What is claimed is:

1. A method adapted to a particle analyzer for discriminating particle groups, the method comprising:
    generating, based on characteristics of particles and particle count within a sample to be measured, a particle characteristic distribution histogram, wherein a first direction coordinate of the particle characteristic distribution histogram indicates channels for representing the characteristics of the particles, and a second direction coordinate indicates the particle count;
    setting a valid area selection height in the particle characteristics distribution histogram, and generating an equivalent negative histogram based on the set height and the particle characteristic distribution histogram, wherein a height value of a bar in the equivalent negative histogram for a certain channel equals the valid area selection height minus a height value of a bar in the particle characteristic histogram for said channel;
    processing the equivalent negative histogram by using an equation $$M_k = \frac{\int x \cdot g(f(x))dx}{\int g(f(x))dx}$$

to obtain a dividing line between the particle groups,
    where $M_k$ is the dividing line between the particle groups;
        x is a channel value in the equivalent negative histogram;
        f(x) is a height value of a bar in the equivalent negative histogram for channel x; and
        g(•) is a processing function with the following features:

$\forall x \geq y \geq 0, g(x) \geq g(y) \geq 0$ $\forall x < 0, g(x) = 0$.

2. The method of claim 1, wherein the characteristic of the particles is the volume size of the particles.

3. The method of claim 2, wherein the valid area selection height is lower than a maximum of the particle count for a particle group having fewer particles.

4. The method of claim 3, wherein the equivalent negative histogram has the same number of channels as the particle characteristic distribution histogram, and each of the channels in the equivalent negative histogram has the same meaning as that in the particle characteristic distribution histogram.

5. The method of claim 4, wherein the equivalent negative histogram only has valid values in a dividing area between two particle groups, and has zeros for other channels.

6. The method of claim 1, wherein the sample to be measured is a blood sample, the particle analyzer is a hematology analyzer, and the particle groups to be discriminated includes a group of platelets and a group of red blood cells, or includes a group of lymphocytes and a group of granulocytes.

7. The method claim 1, further comprising the initial steps of:
    driving a mixture of the sample to be measured and a diluent through an aperture by a driving power source;
    using the particle analyzer to capture a voltage pulse generated when each particle is passing through the aperture;
    calculating, by the particle analyzer, the volume of each particle and calculating the particle count corresponding to the same volume based on the captured voltage pulses.

8. A particle analyzer for discriminating particle groups, comprising:
    a histogram generating unit, for generating, based on characteristics of particles and particle count within a sample to be measured, a particle characteristic distribution histogram, wherein a first direction coordinate of the particle characteristic distribution histogram indicates channels for representing the characteristics of the particles, and a second direction coordinate indicates the particle count;
    a valid area selection height generation unit, for setting a valid area selection height in the particle characteristic distribution histogram, and
    an equivalent negative histogram generation unit, for generating an equivalent negative histogram based on the valid area selection height and the particle characteristic distribution histogram, wherein a height value of a bar in the equivalent negative histogram for a certain channel equals the valid area selection height minus a height value of a bar in the particle characteristic histogram for said channel;
    a dividing line determination unit, for processing the equivalent negative histogram by using an equation $$M_k = \frac{\int x \cdot g(f(x))dx}{\int g(f(x))dx}$$

to obtain a dividing line between the particle groups,
    where $M_k$ is the dividing line between the particle groups;
        x is a channel value in the equivalent negative histogram;
        f(x) is a height value of a bar in the equivalent negative histogram for channel x; and
        g(•) is a processing function with the following features:

$\forall x \geq y \geq 0, g(x) \geq g(y) \geq 0$ $\forall x < 0, g(x) = 0$.

9. The particle analyzer of claim 8, wherein the characteristic of the particles is the volume size of the particles, and the valid area selection height is lower than a maximum of the particle count for a particle group having fewer particles.

10. A particle analyzer for discriminating particle groups, comprising:
    an aperture structure, through which a mixture of a sample to be measured and an electrically conductive diluent is driven to pass by a driving power source;
    a data capturing unit, for capturing a voltage pulse generated when each particle is passing through the aperture;
    a data statistic calculation unit, for calculating, based on the captured voltage pulses, the volume of each particle and particle count corresponding to the same volume;
    a histogram generating unit, for generating, based on the characteristics of particles and particle count within a sample to be measured, a particle characteristic distribution histogram, wherein a first direction coordinate of the particle characteristic distribution histogram indicates channels for representing the characteristics of the particles, and a second direction coordinate indicates the particle count;

a valid area selection height generation unit, for setting a valid area selection height in the particle characteristic distribution histogram; and an equivalent negative histogram generation unit, for generating an equivalent negative histogram based on the valid area selection height and the particle characteristic distribution histogram, wherein a height value of a bar in the equivalent negative histogram for a certain channel equals the valid area selection height minus a height value of a bar in the particle characteristic histogram for said channel;

a dividing line determination unit, for processing the equivalent negative histogram by using an equation $$M_k = \frac{\int x \cdot g(f(x))dx}{\int g(f(x))dx}$$

to obtain a dividing line between the particle groups, where $M_k$ is the dividing line between the particle groups;
x is a channel value in the equivalent negative histogram;
f(x) is a height value of a bar in the equivalent negative histogram for channel x;
g(•) is a processing function with the following features:

$\forall x \geq y \geq 0, g(x) \geq g(y) \geq 0$ $\forall x < 0, g(x) = 0$.

11. A computer-readable medium comprising program code for performing a method for discriminating particle groups, the method comprising:

generating, based on characteristics of particles and particle count within a sample to be measured, a particle characteristic distribution histogram, wherein a first direction coordinate of the particle characteristic distribution histogram indicates channels for representing the characteristics of the particles, and a second direction coordinate indicates the particle count;

setting a valid area selection height in the particle characteristics distribution histogram, and generating an equivalent negative histogram based on the set height and the particle characteristic distribution histogram, wherein a height value of a bar in the equivalent negative histogram for a certain channel equals the valid area selection height minus a height value of a bar in the particle characteristic histogram for said channel;

processing the equivalent negative histogram by using an equation $$M_k = \frac{\int x \cdot g(f(x))dx}{\int g(f(x))dx}$$

to obtain a dividing line between the particle groups, where $M_k$ is the dividing line between the particle groups;
x is a channel value in the equivalent negative histogram;
f(x) is a height value of a bar in the equivalent negative histogram for channel x;
g(•) is a processing function with the following features:

$\forall x \geq y \geq 0, g(x) \geq g(y) \geq 0$ $\forall x < 0, g(x) = 0$.

12. The computer-readable medium of claim 11, wherein the characteristic of the particles is the volume size of the particles.

13. The computer-readable medium of claim 12, wherein the valid area selection height is lower than a maximum of the particle count for a particle group having fewer particles.

14. The computer-readable medium of claim 13, wherein the equivalent negative histogram has the same number of channels as the particle characteristic distribution histogram, and each of the channels in the equivalent negative histogram has the same meaning as that in the particle characteristic distribution histogram.

15. The computer-readable medium of claim 14, wherein the equivalent negative histogram only has valid values in a dividing area between two particle groups, and has zeros for other channels.

16. The computer-readable medium of claim 11, wherein the sample to be measured is a blood sample and the particle groups to be discriminated includes a group of platelets and a group of red blood cells, or includes a group of lymphocytes and a group of granulocytes.

17. The computer-readable medium claim 11, wherein the method further comprises the initial steps of:

driving a mixture of the sample to be measured and a diluent through an aperture by a driving power source;
capturing a voltage pulse generated when each particle is passing through the aperture;
calculating the volume of each particle and calculating the particle count corresponding to the same volume based on the captured voltage pulses.

18. An apparatus for discriminating particle groups comprising:

means for generating, based on characteristics of particles and particle count within a sample to be measured, a particle characteristic distribution histogram, wherein a first direction coordinate of the particle characteristic distribution histogram indicates channels for representing the characteristics of the particles, and a second direction coordinate indicates the particle count;

means for setting a valid area selection height in the particle characteristics distribution histogram, and generating an equivalent negative histogram based on the set height and the particle characteristic distribution histogram, wherein a height value of a bar in the equivalent negative histogram for a certain channel equals the valid area selection height minus a height value of a bar in the particle characteristic histogram for said channel;

means for processing the equivalent negative histogram by using an equation $$M_k = \frac{\int x \cdot g(f(x))dx}{\int g(f(x))dx}$$

to obtain a dividing line between the particle groups, where $M_k$ is the dividing line between the particle groups;
x is a channel value in the equivalent negative histogram;
f(x) is a height value of a bar in the equivalent negative histogram for channel x; and
g(•) is a processing function with the following features:

$\forall x \geq y \geq 0, g(x) \geq g(y) \geq 0$ $\forall x < 0, g(x) = 0$.

19. The apparatus of claim 18, wherein the characteristic of the particles is the volume size of the particles.

20. The apparatus of claim 19, wherein the valid area selection height is lower than a maximum of the particle count for a particle group having fewer particles.

21. The apparatus of claim 20, wherein the equivalent negative histogram has the same number of channels as the particle characteristic distribution histogram, and each of the channels in the equivalent negative histogram has the same meaning as that in the particle characteristic distribution histogram.

22. The apparatus of claim 21, wherein the equivalent negative histogram only has valid values in a dividing area between two particle groups, and has zeros for other channels.

23. The apparatus of claim 18, wherein the sample to be measured is a blood sample, the particle analyzer is a hematology analyzer, and the particle groups to be discriminated includes a group of platelets and a group of red blood cells, or includes a group of lymphocytes and a group of granulocytes.

24. The apparatus claim 18, wherein the method further comprises the initial steps of:
- means for driving a mixture of the sample to be measured and a diluent through an aperture by a driving power source;
- means for capturing a voltage pulse generated when each particle is passing through the aperture;
- means for calculating the volume of each particle and calculating the particle count corresponding to the same volume based on the captured voltage pulses.

* * * * *